United States Patent [19]

Janocha et al.

[11] 4,139,518

[45] Feb. 13, 1979

[54] POLYETHYLENE TEREPHTHALATE COMPOSITION AND SHAPED ARTICLES

[75] Inventors: Siegfried Janocha, Wiesbaden-Biebrich; Manfred Unger, Schlangenbad; Klaus Hoheisel, Wiesbaden-Biebrich, all of Fed. Rep. of Germany

[73] Assignee: Hoechst Aktiengesellschaft, Frankfurt am Main, Fed. Rep. of Germany

[21] Appl. No.: 818,018

[22] Filed: Jul. 22, 1977

[30] Foreign Application Priority Data

Jul. 24, 1976 [DE] Fed. Rep. of Germany ....... 2633358

[51] Int. Cl.² .......................... C08K 3/36; C08K 5/09
[52] U.S. Cl. .......................... 260/40 R; 260/DIG. 35; 528/274
[58] Field of Search ........... 260/40 R, 75 R, DIG. 35

[56] References Cited

U.S. PATENT DOCUMENTS

| 3,024,220 | 3/1962 | Cramer | 260/75 R |
| 3,821,156 | 6/1974 | Farcar | 260/40 R |

FOREIGN PATENT DOCUMENTS

49-21100  5/1974 Japan ................... 260/40 R
951768  3/1964 United Kingdom.

*Primary Examiner*—Sandra M. Person
*Attorney, Agent, or Firm*—Bacon & Thomas

[57] ABSTRACT

Disclosed is a composition, comprising a calcium-containing polyethylene terephthalate polymer and from about 0.01 to 1% by weight of silica obtained by a pyrogenic process, as well as a method of producing same and improved shaped articles made from said composition.

21 Claims, 2 Drawing Figures

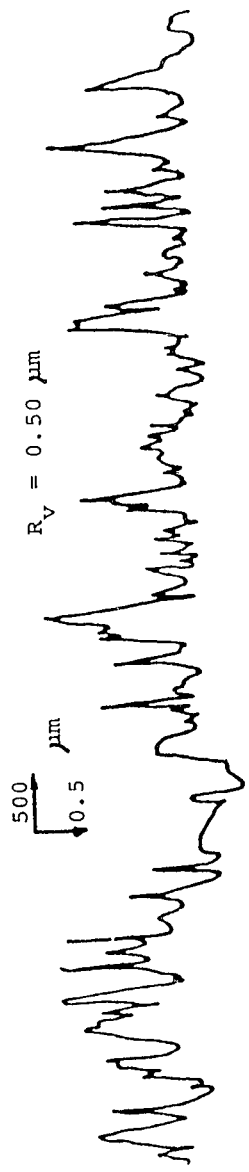
FIG. 1  $R_v = 0.50 \ \mu m$
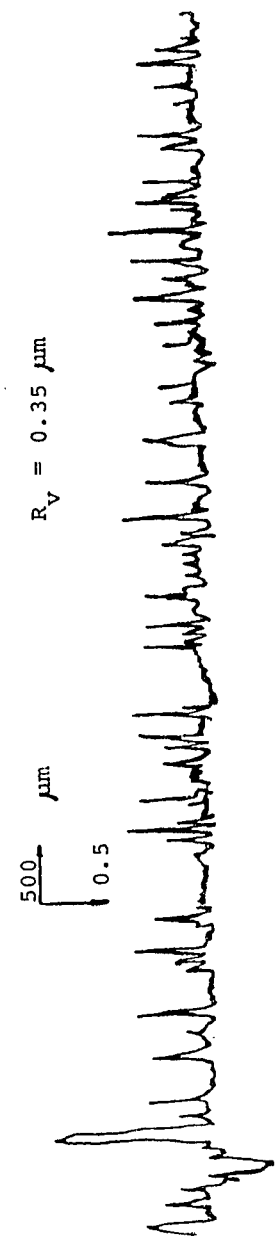
FIG. 2  $R_v = 0.35 \ \mu m$

POLYETHYLENE TEREPHTHALATE COMPOSITION AND SHAPED ARTICLES

BACKGROUND OF THE INVENTION

The present invention relates to a new polyethylene terephthalate raw material, to a process for its manufacture, and to its use.

The preparation of polyethylene terephthalate by polycondensation, with the use of catalysts, such as antimony oxides, has been well known for a long time and need not be described in detail. Furthermore, it is well known in the prior art to add catalysts, e.g., calcium, lithium, manganese or zinc salts, during the interchange of ester radicals which precedes polycondensation. The catalysts are mainly chosen with the objective in mind of achieving an economical preparation of the raw material, faster reaction times, favorable color shades, and the like.

In addition it is known from British Pat. No. 951,768 to add pigments, such as calcium carbonate, calcium silicates, glass, titanium dioxide, or silicium dioxide to polymers, e.g., polyethylene terephthalate, for the manufacture of films, with the quantities added ranging from 1 to 25 percent by weight. The particle size of the pigments may range from 0.3 to 20 $\mu$m. Depending on their type, grain size, and quantity, the pigments added change the physical properties of the resulting film, which may become either matte or transparent in appearance. In some cases, by this addition, the surface of the film is modified in such a way that it is possible to write upon it.

Polyethylene terephthalates prepared with the aid of esterification catalysts possess certain disadvantages, however. After being melted for the preparation of shaped articles, such as films or filaments, some compositions are not easily filterable, or the useful lives of the filters are relatively short, or they tend to form deposits on the walls of the condensation vessel so that coarse impurities may get into the raw material. Shaped articles produced from such raw materials, e.g., films, frequently show spots, as a result of which their usability, for example as condensor films, is considerably impaired.

Furthermore, the depth of roughness of the film and its surface waviness are frequently unsatisfactory, because it is desirable to make the surfaces as even as possible. In this regard, the slip of the film also plays an important role.

SUMMARY OF THE INVENTION

It is an object of the present invention, therefore, to provide an improved polyethylene terephthalate raw material.

It is a particular object of the present invention to provide a polyethylene terephthalate raw material which does not have the above-mentioned disadvantages of the hitherto known raw materials.

A further object of the invention resides in the provision of a method for producing the afore-mentioned polyethylene terephthalate raw material.

Still another object of the invention is the provision of improved new shaped articles manufactured from the improved polyethylene terephthalate compositions according to the invention.

In accomplishing the foregoing objects, there has been provided in accordance with the present invention a composition, comprising a calcium-containing polyethylene terephthalate polymer and an amount sufficient to enhance the melt filterability of the composition of silica obtained by a pyrogenic process. Preferably, the amount of silica is between about 0.01 and 1% and more preferably between about 0.1 and 0.6% by weight of the composition.

In accordance with another aspect of the invention, there has been provided a process for preparing the above-defined composition, comprising the step of conducting an esterification reaction between polyethylene glycol and terephthalic acid or a lower alkyl ester thereof in the presence of said pyrogenic silica, whereby the effective amount of silica is incorporated into the resulting polyethylene terephthalate polymer. The silica may be either added prior to the beginning of or during the esterification reaction, preferably shortly after the beginning of the esterification reaction.

The invention also provides in accordance with a further aspect thereof a shaped article, comprising the composition as defined above, preferably in the form of a stretched film characterized by improved values for depth of roughness and low values for short-wave length irregularities in film thickness.

Further objects, features and advantages of the invention will become evident from the following detailed description of preferred embodiments.

BRIEF DESCRIPTION OF THE DRAWINGS

In the drawings:

FIG. 1 is a graphical representation of the degree of waviness of a biaxially (longitudinally/transversely) stretched film of calcium-containing polyethylene terephthalate raw material according to the prior art (6 $\mu$m); and FIG. 2 is a similar graphical representation for a biaxially (longitudinally/transversely) stretched film of calcium-containing polyethylene terephthalate raw material according to the invention with 0.6 percent by weight of pyrogenic silica incorporated therein (6 $\mu$m).

DETAILED DESCRIPTION OF PREFERRED EMBODIMENTS

Surprisingly, it was found that a raw material which is superior in its manufacture, processing, and use may be obtained if the polyethylene terephthalate raw material, which contains calcium salts originating from the catalyst, further comprises between 0.01 and 1.0% by weight of pyrogenic silica.

The term "pyrogenic silica" as used herein shall mean a silicon dioxide which is produced by pyrogenic means, e.g., from silicon halides, and which is distinguished by its small particle size. For example, the average particle size of the primary particles of some commercially available types range between about 5 and 50 m$\mu$. Suitable pyrogenic silica are described in the prospectus "Aerosil ®" published by Degussa, Frankfurt, Germany; they are obtained from $SiCl_4$ by hydrolysis at high temperature in a gaseous phase. Among the pyrogenic silica mentioned in said prospectus, the type "Aerosil TT 600" was found to be most advantageous. The average particle size of the primary particles ranges from 20 to 50 m$\mu$, and the surface, measured according to BET standard, is 200±50 m$^2$/g.

Such pyrogenic or synthetic silica are used, for example, to produce or maintain the flowability of adherent powders, such as spices, soap powder, fire extinguisher powders, blasting powder, and the like.

The polyethylene terephthalate raw material according to the present invention preferably contains from about 0.1 to 0.6 percent by weight of pyrogenic silica, because within this range optimum effects are produced as regards filtering capacity, freedom of spots of the shaped bodies produced from the raw material, and favorable depth of roughness and waviness values of the resulting film.

The new polyethylene terephthalate raw material may be prepared in various ways. Thus, it is possible to add the pyrogenic silica prior to or during the known condensation process. Preferably, it is incorporated together with the calcium salt used as the catalyst in a known esterification process or shortly after the onset of esterification. Calcium acetate is preferably used as the esterification catalyst. The calcium salts used as the esterification catalysts are preferably added in such quantities that 0.01 to 0.1 percent by weight of calcium are contained in the polyethylene terephthalate.

Polyethylene terephthalates which may be used are those having an SV-value of from 500 to 1500. Polyethylene terephthalates having an SV-value of from 700 to 900 were found to be particularly suitable. The SV-value is characterized as $\eta rel.-1/c \cdot 1000$, wherein c is 1 g/100 ml at a temperature of 25° C. in a phenol/tetrachloroethane mixture (60 : 40 percent by weight). - The preparation of calcium-containing polyethylene terephthalate is described, for example, in U.S. Pat. No. 3,171,828.

Surprisingly, it has been found that, by the inventive incorporation of pyrogenic silica in the polyethylene terephthalate, the useful life of commercial filters at melting temperatures between 265° and 300° C. and specific viscosities between 600 and 900 may be increased from two to five times. Furthermore, the polycondensation vessels need only be cleaned at intervals which correspond to two- to ten-times the normal cleaning intervals. These facts reduce the number of time-consuming interruptions of the production process.

A further, important advantage becomes obvious in the shaped articles formed from the polyethylene terephthalate raw material according to the invention, such as films or filaments. The shaped bodies are substantially free of spots and are thus of improved quality, a fact which is of great importance for some applications, for example, as films for use as tapes in computers, or as sheets for electrical insulation.

Films prepared from the raw material according to the invention, either by the known tubular stretching process or by the flat stretching process, showed improved depth of roughness and waviness values, as is desirable for good surface properties.

The terms "waviness" and "depth of roughness" require some explanation here, because they serve for a better comprehension of the unexpected improvements achieved by the present invention.

When measuring the surfaces of stretched, preferably biaxially stretched polyethylene terephthalate films by means of commercially available measuring instruments, various degrees of surface irregularities are found:

1. Variations in thickness, which, e.g., are constantly recorded during production control.

These variations consist of wide waves which, as far as possible, are kept within certain tolerable limits. For a film of a theoretical thickness of 20 μm and a width of from 1000 to 3000 mm, the variations in thickness should not exceed 2 μm.

2. Waviness

These variations are surface irregularities within the short-wave length range which may comprise differences in height of from 0.2 to 2.0 μm over short distances. In its upper region, the waviness changes over into the variations in thickness described under 1.), and in its lower region it passes over into the depth of roughness, infra.

3. Depth of Roughness

The depth of roughness may be defined as the microtopography of the surface; it is normally in the range of a few tenths of a μ. Depth of roughness and waviness may be measured by means of commercially available measuring instruments, for example a Perth-o-meter.

It was found that the depth of roughness and the waviness are responsible for very specific properties of the surface. In particular, they influence one another.

Upon examination of a longitudinally/transversely stretched film made of a polyethylene terephthalate raw material containing calcium originating from the esterification catalyst (calcium raw material), strong waviness of the surface of the film becomes apparent. Such a surface is not of optimum quality for, e.g., condensor films. Owing to excess waviness, too much air is trapped between the windings of the condensor, and the depth of roughness is not sufficient to guarantee good slipping qualities in the case of thin films, e.g., within the range below 5 μm.

It was found that the waviness may be completely eliminated or at least reduced by using a raw material according to the invention for the preparation of films, in particular biaxially stretched films. For example, in FIG. 1 is illustrated the waviness of a biaxially (longitudinally/transversely) stretched film of calcium-containing polyethylene terephthalate raw material according to the prior art (6 μm); see Example 2. In comparison, there is illustrated in FIG. 2 the waviness of a biaxially (longitudinally/transversely) stretched film of calcium-containing polyethylene terephthalate raw material according to the invention with 0.6 percent by weight of pyrogenic silica incorporated therein (6 μm); see Example 1. The films were stretched under identical conditions.

EXAMPLE 1

600 parts by weight of dimethyl terephthalate are dissolved, while stirring and heating in a vessel, with 480 parts by weight of ethylene glycol to which 0.0767 percent by weight of calcium acetate and 0.6 percent by weight of pyrogenic silica (type "Aerosil TT 600") have been added, and the mass is then transesterified while methanol is distilled off over a heated reflux condenser. Towards the end of the trans-esterification process, 0.011 percent by weight of $H_3PO_3$, based on the quantity of dimethyl terephthalate used, is added at a temperature between 215° and 250° C. 0.04 percent by weight of $Sb_2O_3$ is added as a condensation catalyst. While the temperature rises, excess ethylene glycol is separated. At a temperature of 225° C., a vacuum is applied and air is evacuated until, finally, a maximum vacuum of 0.3 Torr. is reached. In accordance with a predetermined temperature program, and parallel to the vacuum program, the temperature is gradually increased to 280° C.

The polyethylene terephthalate thus obtained has an SV-value of 810. It is dried, melted in an extruder, and extruded from a slot die at 260° C.. The melt is cooled to 30° C. on a cooling drum. The resulting amorphous pre-film is then stretched in a longitudinal stretching apparatus to 4.5 times its original length at 85° C. and then transversely stretched to 3.3 times its original width at 95° C.

The resulting, 6 μm thick film is thermally fixed for 10 seconds at 200° C. FIG. 2 shows the roughness values measured by means of a Perth-o-meter.

EXAMPLE 2

The procedure described in Example 1 is repeated, with the sole exception that no pyrogenic silica is added. FIG. 1 shows the roughness values determined with a Perth-o-meter.

The reduction of the waviness also becomes apparent from the values indicating the deviations in thickness. Whereas $R_t$ means only the depth of roughening, $W + R_t$ includes the waviness. In the case of the film made from the prior art raw material, these values differ considerably, whereas the corresponding film made from the raw material according to the invention shows only an insignificant increase of the $W + R_t$ value as compared with the $R_t$ value. Reference is made to the data in the following table. - RV is the depth of roughness H as defined on page 5 of the prospectus "Perthometer-OberflächenMeBgeräte", published by Dr.Ing.Perthen GmbH, Hannover, Germany.

| Depth of Roughness | Biaxially (longitudinally/transversely stretched film of calcium-containing raw material corresponding to the prior art 3.5 μm | Biaxially (longitudinally/transversely) stretched film of the raw material according to the invention containing 0.6% by wt. of pyrogenic silica 3.5 μm |
|---|---|---|
| $R_t$ (Depth of roughness) | 0.79 | 0.62 |
| $W + R_t$ | 0.84 | 0.63 |

The two films were stretched under identical conditions. The film made of the raw material according to the invention not only has the advantage of being less wavy, it also has excellent slip properties due to the addition of pyrogenic silica.

The 3.5 μm thick film made of the raw material according to the prior art has a slip value of 1.8, whereas a film made of the raw material of the present invention has a slip value of 0.4.

The examples given above are selected to demonstrate the invention generally, and it is not intended to limit the invention to these examples.

Similar results were obtained when using films of a thickness between 2.5 and 50 μm and pyrogenic silica additions between about 0.1 and 1.0 percent by weight, the best results being obtained, however, with additions between about 0.1 and 0.6 percent by weight.

What is claimed is:

1. A polyester composition characterized by enhanced melt filterability properties and being adapted for producing biaxially oriented film products having improved depth of roughness values and low values for short wave length irregularities in film thickness, said composition consisting essentially of a polyethylene terephthalate polymer, calcium in the form of a salt which is capable of catalyzing the transesterification reaction between dimethyl terephthalate and ethylene glycol, and an amount sufficient to enhance the melt filterability of the composition of silica obtained by a pyrogenic process.

2. The composition as defined by claim 1, wherein the amount of silica is between about 0.01 and 1% by weight of the composition.

3. The composition as defined by claim 1, wherein the amount of silica is between about 0.1 and 0.6% by weight of the composition.

4. The composition as defined by claim 1, wherein said pyrogenic silica is produced by pyrogenic treatment of a silicon halide.

5. The composition as defined by claim 4, wherein said pyrogenic silica is produced by hydrolysis at an elevated temperature of $SiCl_4$ in a gaseous phase.

6. The composition as defined by claim 1, wherein said pyrogenic silica comprises an average particle size of between about 5 and 50 millimicrons.

7. The composition as defined by claim 6, wherein said pyrogenic silica comprises an average particle size of between about 20 and 50 millimicrons.

8. The composition as defined by claim 7, wherein said pyrogenic silica comprises a BET surface area per mass of between about 150 and 250 m$^2$/g.

9. The composition as defined by claim 1, wherein said calcium salt comprises calcium acetate.

10. The composition as defined by claim 1, wherein said calcium salt is present in the polyethylene terephthalate in an amount between about 0.01 and 0.1% by weight.

11. A process for preparing the composition as defined by claim 1, comprising the steps of conducting a transesterification reaction between ethylene glycol and a lower alkyl ester of terephthalic acid in the presence of a catalytically active calcium salt for said reaction, whereby an ester is produced, subjecting said ester to polyester condensation reaction conditions, and incorporating an amount of said pyrogenic silica effective to enhance the melt filterability of the composition at a point in the process not subsequent to said condensation reaction.

12. The process as defined by claim 11, wherein said pyrogenic silica is incorporated prior to the beginning of said esterification reaction.

13. The process as defined by claim 12, wherein said pyrogenic silica is contained in said ethylene glycol.

14. The process as defined by claim 11, wherein said pyrogenic silica is added during said esterification reaction.

15. The process as defined by claim 14, wherein said pyrogenic silica is added shortly after the beginning of said esterification reaction.

16. A shaped article, comprising the composition as defined by claim 1.

17. A shaped article, comprising the composition as defined by claim 2.

18. A shaped article, comprising the composition as defined by claim 4.

19. A stretched film characterized by improved values for depth of roughness and low values for short-wave length irregularities in film thickness, comprising the composition as defined by claim 1.

20. A stretched film characterized by improved values for depth of roughness and low values for short-wave length irregularities in film thickness, comprising the composition as defined by claim 2.

21. A stretched film characterized by improved values for depth of roughness and low values for short-wave length irregularities in film thickness, comprising the composition as defined by claim 4.

* * * * *